United States Patent
Andersen

(10) Patent No.: US 8,728,443 B2
(45) Date of Patent: *May 20, 2014

(54) FORMULATION COMPRISING NICOTINE AND A CATION EXCHANGE RESIN

(75) Inventor: Carsten Andersen, Vejle (DK)

(73) Assignee: Fertin Pharma A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/700,690

(22) PCT Filed: May 31, 2010

(86) PCT No.: PCT/EP2010/057560
§ 371 (c)(1),
(2), (4) Date: Nov. 28, 2012

(87) PCT Pub. No.: WO2011/150959
PCT Pub. Date: Dec. 8, 2011

(65) Prior Publication Data
US 2013/0071338 A1      Mar. 21, 2013

(51) Int. Cl.
*A61K 9/00* (2006.01)
*A61K 9/28* (2006.01)
*A61K 31/465* (2006.01)

(52) U.S. Cl.
USPC ............................................ 424/48; 514/343

(58) Field of Classification Search
USPC ............................................ 424/48; 514/79
See application file for complete search history.

(56) References Cited

U.S. PATENT DOCUMENTS

| | | | |
|---|---|---|---|
| 3,845,217 A | 10/1974 | Fernö et al. | |
| 3,861,402 A * | 1/1975 | Briskin | 131/359 |
| 3,901,248 A | 8/1975 | Lichtneckert et al. | |
| 4,579,858 A | 4/1986 | Fernö et al. | |
| 6,586,449 B1 | 7/2003 | Walling | |

FOREIGN PATENT DOCUMENTS

| | | | |
|---|---|---|---|
| WO | 2005/053691 | | 6/2005 |
| WO | 2006/000232 | | 1/2006 |
| WO | WO-2006-000232 | * | 1/2006 |
| WO | 2006/128468 | | 12/2006 |
| WO | WO-2006-128468 | * | 12/2006 |

OTHER PUBLICATIONS

International Search Report dated Apr. 4, 2011 in Appln No. PCT/EP2010/057560.
European Pharmacopoeia 6.0, vol. 1, 4 pgs.
2009 USP NF The Official Compendia of Standards, Official Monographs, vol. 32, p. 3081, 3 pgs. total.
2003 USP NF The Official Compendia of Standards, Official Monographs, vol. 26, pp. 1309-1310, 3 pgs. total.

* cited by examiner

*Primary Examiner* — Frederick Krass
*Assistant Examiner* — Celeste A Roney
(74) *Attorney, Agent, or Firm* — Merchant & Gould P.C.

(57) ABSTRACT

A method of producing a nicotine delivery product includes a mixture having nicotine, a cation exchange resin and water. The water content of the mixture is between 5 and 75 wt. % relative to the whole mixture. The mixture is combined with further components of the nicotine delivery product.

10 Claims, No Drawings

FORMULATION COMPRISING NICOTINE AND A CATION EXCHANGE RESIN

This application is a National Stage Application of PCT/EP2010/057560, filed 31 May 2010, which application is incorporated herein by reference. To the extent appropriate, a claim of priority is made to each of the above disclosed applications.

FIELD OF THE INVENTION

The present invention relates to the manufacture of nicotine delivery products. In particular the present invention relates to the manufacture of nicotine-containing chewing gum products.

BACKGROUND

Nicotine is a well known, highly characterized alkaloid that can be isolated from the dried leaves of *Nicotiana tabacum*. Its numerous commercial uses include utilities such as a fumigant, an insecticide and the like. It is therapeutically valuable in the treatment of the smoking withdrawal syndrome.

Smoking, e.g., cigarettes, pipes or cigars, results in the uptake of nicotine by the body. As nicotine is a stimulant, the smoker experiences a pleasant sensation arising from the uptake of nicotine in the body—this pleasant sensation is addictive. Whilst nicotine itself may not be particularly harmful to the human body, smoking may be associated with health hazards not necessarily associated with administration of nicotine itself, but e.g. associated with inhalation of tar.

As a result, non-smoking methods have been devised to administer nicotine to the body. These include nicotine-containing chewing gums, nicotine-impregnated dermal patches, nicotine inhalers and the like. A variety of patents have disclosed such products.

Incorporation of nicotine in its pure form into a nicotine delivery product has turned out not to be advantageous, because nicotine is relatively volatile so that the resulting nicotine delivery products are not always adequately stable, losing nicotine relatively rapidly over time.

One advance has been the development of nicotine polacrilex resins (NPR), where nicotine molecules are bound to a cationic exchange resin. Using an NPR instead of nicotine base in a nicotine delivery product significantly improves the product's stability. Adequate release is also possible. NPR is used e.g. in various nicotine-containing chewing gum compositions.

U.S. Pat. No. 6,586,449 claims a method for preparing a nicotine-containing composition having a nicotine release rate of not less than 70% over a 10 minute period said method comprising (a) mixing an aqueous solution of an organic polyol with a cation exchange resin selected from the group consisting of (i)—a methacrylic, weakly acidic type of resin containing carboxylic functional groups, (ii)—a polystyrene, strongly acidic type of resin containing sulphonic functional groups, and (iii)—a polystyrene, intermediate acidic type of resin containing phosphonic functional groups, thereby forming a cation exchange resin mixture having some of its ion exchange sites partially blocked with said polyol; (b) admixing with said mixture of step (a) an aqueous solution of nicotine to form a nicotine-coated cation exchange resin admixture; and (c) removing water from said admixture to produce said nicotine composition having a nicotine release rate of not less than 70% over a 10 minute period. The resulting dry nicotine composition can presumably be used to manufacture a nicotine delivery product such as a nicotine-containing chewing gum, by mixing the dry nicotine composition with further ingredients such as gum base and a sweetener.

When mixing a cation exchange resin, a polyol, and nicotine, U.S. Pat. No. 6,586,449 teaches preparation of an aqueous slurry as an intermediate and the removal of water for isolating the nicotine composition. The step of removing water is considered by U.S. Pat. No. 6,586,449 to be essential, and its prior art discussion makes it clear that its author considered that any nicotine-containing system which comprises water must be unstable.

A disadvantage of the prior art method for producing a nicotine-containing composition is that it is time consuming as a consequence of the water-removal step, which also requires a considerable amount of energy to be expended. Furthermore, the amounts of water needed reduces the capacity of a given production plant. The amount of water removed to produce the nicotine delivery product is above 90% by weight of added water and the water content of the nicotine delivery product after removal of water is typically only a few percent by weight of the nicotine delivery. Finally, the dry NPR has a tendency to dust when no polyol is used.

The present invention aims to solve the aforementioned deficiencies of the prior art, by providing a method of manufacturing a nicotine delivery product (such as nicotine-containing chewing gums, nicotine-containing lozenges, nicotine-containing pastilles, nicotine-containing tablets, nicotine-containing patches, nicotine-containing inhalers and nicotine-containing nasal sprays) which method is simpler, faster and/or more energy-efficient than the methods known from the prior art.

SUMMARY OF THE INVENTION

Accordingly there is provided a method of producing a nicotine delivery product, the method comprising:
combining (i) a mixture comprising nicotine, a cation exchange resin and water, wherein the water content of the mixture is between 5 and 75 wt. % relative to the whole mixture; and (ii) further components of the nicotine delivery product.

DETAILED DESCRIPTION

It has now surprisingly been found that a more simple and efficient way of producing a nicotine delivery product may be provided. Contrary to all expectation, the resulting nicotine delivery product according to the present invention has an acceptable stability and release profile despite the fact that a relatively wet nicotine composition is used in the manufacture of the nicotine delivery product.

An additional advantage of using a wet nicotine composition is that it is not necessary to include a C2 to C12 linear or branched hydrocarbon having at least 2 hydroxyl groups, such as glycerol. Inclusion of glycerol is advantageous in the context of dry nicotine compositions because it reduces the dusting tendency of the dry nicotine composition. However, the inclusion of such a component is not required in a wet nicotine composition as these do not dust. In a preferred embodiment of the present invention, the mixture (i) does not comprise a C2 to C12 linear or branched hydrocarbon having at least 2 hydroxyl groups, such as glycerol.

Although water removal is not necessary in the method of the present invention, some water may be removed from the mixture (i) provided that 5-75 wt. % of the resulting dried mixture is water. If a drying step is used, up to 80 wt. % of the water present in the mixture may be removed, such as 1-75 wt. %, 1-50 wt. %, or 1-10 wt. %. If drying is carried out, temperatures in excess of 75-80° C. should be avoided as this may cause loss of nicotine. Preferably, the temperature should be kept below 60° C.

It has surprisingly been found that the nicotine delivery products obtained by the process of the present invention have at least the same properties as those obtained by incorporating the compositions disclosed in U.S. Pat. No. 6,586,449 in a similar delivery product. The mixture (i) referred to in claim 1 of this application can have at least as high a release rate of nicotine as the compositions of U.S. Pat. No. 6,586,449, i.e. at least 70% over a 10 minute period when determined as described in more detail in the U.S.P. Official Monograph, Volume 26, pages 1309-1310.

1. DEFINITIONS

In the context of the present invention, the meaning of "mixture" is different to the meaning of "nicotine delivery product". "Mixture" means an intermediate product, while "nicotine delivery product" refers to a product for end use, such as the nicotine-containing chewing gums.

2. THE NICOTINE DELIVERY PRODUCT

The nicotine delivery product produced with the method of the present invention may e.g. be a nicotine-containing chewing gum, a nicotine-containing lozenge, a nicotine-containing pastil, nicotine-containing tablet, a nicotine-containing patch, a nicotine-containing inhaler or a nicotine-containing nasal spray. The person skilled in the art knows how to formulate such delivery products.

The nicotine delivery product of the invention is preferably a chewing gum. A number of such chewing gums are described in e.g. WO 2006/000232 A1. The chewing gum may comprise additional polyols.

Examples of such polyols are:
C3 polyols such as 1,2 Propanediol (propylene glycol), 1,3 propanediol (trimethylene glycol), and 1,2,3 propanetriol (glycerol); C4 polyols such as Erythritol; C5 polyols such as Xylitol; C6 polyols such as Sorbitol, mannitol, 1,6 hexanediol, or cyclohexanehexol (inositol); and C12 polyols such as Maltitol, maltitol syrup, lactitol, or isomalt; Mono- and disaccharides, Glucose, glucose syrup, fructose, or sucrose.

Reference is made to U.S. Pat. No. 3,845,217 which is incorporated by reference, which shows one possible way to produce a nicotine-containing chewing gum.

3. THE MIXTURE

3.1 Cationic Ion Exchange Resin

Any cationic ion exchange resin may in principle be used in the present invention. Preferably, a non-ionic pharmaceutical grade resin is used. The resin is capable of binding anionic molecules at the ion exchange sites may be employed in the present invention. Examples of such cationic materials are: those bearing a carboxylic acid group, such as a weakly acidic type of resins containing carboxylic functional groups (these resins are typically derived from polymers or copolymers of methacrylic acid or polymethacrylic acid); the strongly acidic type of resins containing sulphonic functional groups (these resins are typically derived from polymers of styrene or copolymers of styrene and divinylbenzene); or the intermediate acidic type of resins containing phosphonic acid functional groups (these resins are typically derived from polymers of styrene or copolymers of styrene and divinylbenzene).

Cationic ion exchange resins are well known in the art and the present invention encompasses all of these. A preferred cation exchange resin is a methacrylic, weakly acidic type of resin containing carboxylic functional groups. Representative cation exchange resins suitable for use in accordance with the present invention are disclosed in U.S. Pat. No. 3,901,248. The preferred cation exchange resins are those known in the art as the Amberlite® resins from Rohm and Haas, Paris, Cedex, France and include, for example, Amberlite® IR20, Amberlite® IRP69, Amberlite® IRP64, Amberlite® IRP58, Amberlite® IRC50, and Amberlite® IRP69. Preferred cation exchange resins are polacrilex ion exchange resin (Amberlite® IRP64) and a weak acidic exchange resin Purolite C115HMR from Purolite.

The cation exchange resin may be selected from the group consisting of (i) a methacrylic, weakly acidic type of resin containing carboxylic functional groups such as polacrilex (Amberlite® IRP64) (ii) a polystyrene, strongly acidic type of resin containing sulphonic functional groups, and (iii) a polystyrene, intermediate acidic type of resin containing phosphonic functional groups.

3.2 Water Content

The mixture used in the method of the present invention has a water content of 5.75 wt. %. Preferably, the water content is 10-75 wt. %, more preferably 15-65 wt. %, even more preferably 20-55 wt. %, and most preferably 25-45 wt. %.

Preferably, the above-mentioned water content is arrived at by mixing the cationic resin, water and nicotine without the use of any drying step. This allows the energy otherwise required to drive off the water to be saved.

In a preferred embodiment of the invention, the water content of the mixture is 25-45 wt. % of the mixture, such as around 35%, and water is not removed from the mixture by drying.

3.3 Nicotine

Nicotine is an essential component of the mixture. It may be used in its base form, or in the form a pharmaceutically acceptable salt, salvate or complex. Preferably nicotine base is used.

The concentration of nicotine in the mixture is preferably between 5 and 50% by weight of the mixture.

3.4 Composition of the Mixture

The weight ratio of the cationic ion exchange resin to nicotine is preferably from 1:1 to 10:1, more preferably from 2:1 to 8:1, and most preferably 4:1.

The mixture may further comprise an organic polyol which is a non-toxic C2 to C12 linear or branched hydrocarbon having at least 2 hydroxyl groups, such as glycerol.

Suitable organic polyols for use according to the present invention are non-toxic C2 to C12 linear or branched hydrocarbons having at least 2 hydroxyl groups preferably selected from the group consisting of 1,2-propanediol, 1,3-propanediol, 1,6-hexanediol, glycerol and sorbitol and non-toxic C5 to C12 cyclic or heterocyclic hydrocarbons having at least 2 hydroxyl groups, preferably selected from the group consisting of hexahydroxyl cyclohexane (inositol) and mono- and disaccharides.

Preferred cyclic or heterocyclic organic polyols are glucose, fructose and sucrose.

When the mixture comprises an organic polyol, this is preferably present in an amount so as to achieve a polyol:resin weight ratio in the range 1:0.8 to 1:7.2, preferably 1:1 to 1:4, most preferably 1:2.4.

The mixture may be produced by a method which comprises a step (a) of mixing nicotine, a cation exchange resin and water. The organic polyol may be added to the mixture before or after nicotine is added. Thus, the mixture may be produced by combining a polyol with a first pre-mix comprising nicotine and the cationic exchange resin. In this way, the organic polyol is combined with the cationic exchange resin after nicotine. Alternatively, the organic polyol may be combined with a second pre-mix comprising the cation exchange resin, said second pre-mix being free of nicotine. Proceeding in this manner means that the glycerol is combined with the cation exchange resin before nicotine is added.

EXAMPLES

The following Examples illustrate the present invention. These Examples should not be regarded as limiting the invention in any sense.

Materials and Methods
Nicotine: in accordance with USP
Water: Purified in accordance with USP Equipment
E1: A 60 liter planetary Bear Varimixer mixer equipped with a beater and scraper.
E2: A sealable Diosna Multi Mixer VAC 150 having a cylindrical mixing vessel of 150 liters equipped with scraper and stirrer and a "chopper" for comminuting agglomerates and lumps. Furthermore, the lid is provided with a temperature sensor stretching into the product mass and a vacuum outlet having a filter. Introduction of air is effected in the bottom of the mixer. At the bottom of the mixer is an outlet for withdrawal of product.
E3: A sealable Diosna Multi Mixer VAC 20 having a cylindrical mixing vessel of 20 liters equipped with scraper and stirrer and a "chopper" for comminuting agglomerates and lumps. Furthermore, the lid is provided with a temperature sensor stretching into the product mass and a vacuum outlet having a filter. Introduction of air is effected in the bottom of the mixer. At the bottom of the mixer is an outlet for withdrawal of product.
E4: A Stephan mixer (vacuum premixing)
E5: A Quadro mill.

Process
P1: A mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.
P1A: Glycerol is added to the product after the addition of nicotine and Amberlite resin. Glycerol was weighed and added to the mixture and stirred for at least 5 minutes before the process was stopped.
P1B: Glycerol is added to the product before the addition of nicotine. Glycerol was weighed and added together with the initial water and stirred for 1 minute. Then ion exchange resin Amberlite® IRP64 was weighed and added to the mixer. The mixer was closed and stirred at least 2 hours at ambient temperature. Finally nicotine is added and stirred for 10 minutes
P2: A mixer was charged with water, and nicotine was weighed and added, The mixer was closed and stirred for 5 minutes. Then ion exchange resin Amberlite® IRP64 was weighed and added to the mixer. The mixer was closed and stirred for 10-60 minutes. Vacuum was connected and the mixture was dried by heating to maximum 60° C. under vacuum at a pressure of about 30-100 mbar (about 25-75 mmHg) with stirring. The drying process was stopped when the temperature reached the specified product temperature.
P2A: Glycerol is added to the product, after the addition of nicotine and Amberlite resin. Glycerol was weighed and added to the mixture and stirred for at least 5 minutes before the process was stopped or drying was started.
P2B: Glycerol is added to the product before the addition of nicotine. Glycerol was weighed and added together with the initial water and stirred for 1 minute. Then ion exchange resin Amberlite® IRP64 was weighed and added to the mixer. The mixer was closed and stirred at least 2 hours at ambient temperature. Finally nicotine is added and stirred for 10 minutes For all the processes, the product was removed from the mixer through the Quadro mill E5 if necessary and sieved if necessary.

The product could be transferred directly to a chewing gum manufacturing process or other products processes. It could also be packed and stored in fibre drums having a PE/alu foil lining and sealed by welding.

Procedure for Determining the Release Rate of Nicotine

The determination of release of nicotine from the mixture was carried out according to the procedure set forth in the U.S.P. Official Monograph, Volume 32, page 3081. The release rate from chewing gum products comprising the mixture was carried out according to the procedure set forth in the Ph. Eur. 6. th ed.

Procedure for Determining the Stability of the Nicotine Delivery Product

As the mixture will, typically, in practice, be used within a week of its production, only experiments running for 1-2 weeks have been made. The samples have been stored under ambient conditions: storage in small containers with loose-fitting lid at laboratory temperature and humidity conditions (approx. 20° C. and 50% RH) for 2 weeks. The samples are analysed for content of nicotine.

In addition, the stability of the delivery product is evaluated as the stability of the finished chewing gum formulation. This stability is evaluated by measuring the content of nicotine at different times under storage at specified controlled conditions.

Example 1 (Reference)

Using the procedure stated above, a mixture of nicotine and cation exchange resin and glycerine of the state of the art was produced from the constituents stated in the below Table 1.

TABLE 1

The mixture was made according to process P2B using equipment E3.
The total process time was 20 minutes. The drying time until
reaching the maximum temperature was about 5 hours 25 min.
After removal of water the composition was:

| Constituent | Amount (kg) | Amount (%) |
| --- | --- | --- |
| Nicotine | 0.60 | 6.0 |
| Water | 0.05 | 1.3 |
| Resin | 2.40 | 24.0 |
| Glycerol | 1.00 | 10.0 |
| Total | 4.05 | 100.0 |
| Nicotine | 0.60 | 6.0 |
| Water | 6.00 | 60.0 |
| Resin | 2.40 | 24.0 |
| Glycerol | 1.00 | 10.0 |
| Total | 10.00 | 100.0 |

| | |
|---|---|
| Total Amount after water removal: | 4.05 kg |
| Nicotine:resin weight ratio: | 1:4 |
| % water removal: | 99.2 |
| % water in mixture: | 1.3 |

Example 2

Using the procedure stated above a mixture of nicotine and cation exchange resin was produced from the constituents stated in the below Table 2.

TABLE 2

| Constituent | Amount (kg) | Amount (%) |
|---|---|---|
| Nicotine | 1.0 | 5.7 |
| Water | 12.5 | 71.4 |
| Resin | 4.0 | 22.9 |
| Total | 17.5 | 100.0 |

| | |
|---|---|
| Total Amount after water removal: | 10.2 kg |
| Nicotine:resin ratio: | 1:4 |
| % water removal: | 58.4 |
| % water in nicotine delivery product: | 51.0 |

The product was made according to process P2 using equipment E4. The total process time was 4 hour 35 min. minutes. After removal of water the composition was:

| | Amount kg | % |
|---|---|---|
| Nicotine | 1.0 | 9.8 |
| Water | 5.2 | 51.0 |
| Resin | 4.0 | 39.2 |
| Total Amount Added | 10.2 | 100.0 |

Example 3

Using the procedure P1 and the equipment E1 stated above a mixture of nicotine and cation exchange resin was produced from the constituents stated in the below Table 3.

TABLE 3

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

| | |
|---|---|
| Nicotine:resin ratio: | 1:4 |
| % water in nicotine delivery product | 34.1 |

The total process time was 20 minutes.

Example 4

Using the procedure P1 and the equipment E1 stated above a mixture of nicotine and cation exchange resin was produced from the constituents stated in the below Table 4

TABLE 4

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

| | |
|---|---|
| Nicotine:resin ratio | 1:4 |
| % water in nicotine delivery product | 7.5 |

The total process time was 20 minutes.

Example 5

Using the procedure P1 and the equipment E1 stated above a mixture of nicotine and cation exchange resin was produced from the constituents stated in the below Table 5.

TABLE 5

| Constituent | Amount (kg) | Amount (%) |
|---|---|---|
| Nicotine | 1.08 | 10.0 |
| Water | 5.40 | 50.0 |
| Resin | 4.32 | 40.0 |
| Total | 10.8 | 100.0 |

| | |
|---|---|
| Nicotine:resin ratio | 1:4 |
| % water in nicotine delivery product | 50.0 |

The total process time was 20 minutes.

Example 6

Using the procedure P1 and the equipment E1 stated above a mixture of nicotine and cation exchange resin was produced from the constituents stated in the below Table 6.

TABLE 6

| Constituent | Amount (kg) | Amount (%) |
|---|---|---|
| Nicotine | 1.08 | 6.0 |
| Water | 12.60 | 70.0 |
| Resin | 4.32 | 24.0 |
| Total | 18.00 | 100.0 |

| | |
|---|---|
| Nicotine:resin ratio | 1:4 |
| % water in nicotine delivery product | 70.0 |

The total process time was 20 minutes.

Example 7

Using the procedure P1 and equipment E1 stated above a mixture of nicotine and cation exchange resin was produced from the constituents stated in the below Table 7.

TABLE 7

| Constituent | Amount (kg) | Amount (%) |
|---|---|---|
| Nicotine | 1.08 | 17.0 |
| Water | 0.95 | 15.0 |
| Resin | 4.32 | 68.0 |
| Total | 6.35 | 100.0 |

| | |
|---|---|
| Nicotine:resin ratio | 1:4 |
| % water in nicotine delivery product | 15.0 |

The total process time was 20 minutes.

Example 8

Using the procedure P2 and the equipment E3 and E5 stated above a mixture of nicotine and cation exchange resin was produced from the constituents stated in the below Table 8.

TABLE 8

| Constituent | Amount (kg) | Amount (%) |
|---|---|---|
| Nicotine | 1.08 | 6.0 |
| Water | 12.60 | 70.0 |
| Resin | 4.32 | 24.0 |
| Total | 18.00 | 100.0 |

| | |
|---|---|
| Total Amount after water removal | 8.55 |
| Nicotine:resin ratio | 1:4 |
| % water removed of water added | 75.0 |
| % water in nicotine delivery product | 36.8 |

The drying time until reaching the maximum temperature was about 2 hours 15 min.

After removal of water the composition was:

| Constituent | Amount (kg) | Amount (%) |
|---|---|---|
| Nicotine | 1.08 | 9.8 |
| Water | 3.15 | 51.0 |
| Resin | 4.32 | 39.2 |
| Total | 8.55 | 100.0 |

Example 9

Using the procedure P2 and the equipment E3 and E5 stated above a mixture of nicotine and cation exchange resin according to the invention was produced from the constituents stated in the below Table 9.

TABLE 9

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

| | |
|---|---|
| Total Amount after water removal | 6.52 |
| Nicotine:resin ratio | 1:4 |
| % water removed of water added | 60.0 |
| % water in nicotine delivery product | 17.2 |

The drying time until reaching the maximum temperature was about 1 hour 45 min.

After removal of water the composition was:

| Composition | Amount (kg) | Amount (%) |
|---|---|---|
| Nicotine | 1.08 | 17.7 |
| Water | 1.12 | 17.2 |
| Resin | 4.32 | 70.8 |
| Total | 6.52 | 100.0 |

Example 10

Using the procedure P2 and the equipment E3 and E5 stated above a mixture of nicotine and cation exchange resin according to the invention was produced from the constituents stated in the below Table 10.

TABLE 10

| Constituent | Amount (kg) | Amount (%) |
|---|---|---|
| Nicotine | 1.08 | 17.0 |
| Water | 0.95 | 15.0 |
| Resin | 4.32 | 68.0 |
| Total | 6.35 | 100.0 |

| | |
|---|---|
| Total Amount after water removal | 5.64 |
| Nicotine:resin ratio | 1:4 |
| % water removed of water added | 75.0 |
| % water in nicotine delivery product | 4.2 |

The drying time until reaching the maximum temperature was about 55 min.

After removal of water the composition was:

| Composition | Amount kg | % |
|---|---|---|
| Nicotine | 1.08 | 19.2 |
| Water | 0.24 | 4.2 |
| Resin | 4.32 | 76.6 |
| Total | 5.64 | 100.0 |

Example 11

Using the procedure stated above, the release of nicotine from a mixture as used according to the invention was compared with the release from a mixture according to the state of the art. The results are stated in the below Table 11.

TABLE 11

| Product | Release (%) |
|---|---|
| Example 1 | 79 |
| Example 2 | 82 |
| Example 3 | 81 |
| Example 4 | 81 |
| Example 5 | 77 |
| Example 6 | 82 |
| Example 7 | 80 |
| Example 8 | 78 |
| Example 9 | 77 |
| Example 10 | 83 |

As it appears, the release of nicotine from the product of the invention is far above the limit of 70% and about the same as from the product made according to the state of the art.

Example 12

The products made according to example 1-10 are used in production of conventional chewing gums.

A typical formula for a full scale production is:

| | |
|---|---|
| Gum base | 360 kg |
| Sorbitol | 93 kg |
| Nicotine mixture | 11.2 kg |
| Sodium carbonate | 10.0 kg |
| Sodium hydrogencarbonate | 5.0 kg |
| Glycerin | 3.5 kg |
| Intense sweeteners | 2.1 kg |
| Liquid flavour | 15.2 kg |
| Total: | 500 kg |

Gum base is added to warm (45°-50° C.) sigma blade gum mixer. Start the mixer and mix for 10 minutes.
Start the mixer and add ⅓ of the Sorbitol. Once the Sorbitol is added, mix for 10 minutes.
Stop the mixer and add the Nicotine Polacrilex blend to the batch. Mix for 2 minutes
Stop the mixer add the intense sweeteners, and mix for 3 minutes.
Stop the mixer and add next ⅓ of sorbitol and mix for 4 minutes.
Stop the mixer and add Sodium Carbonate, anhydrous and Sodium Hydrogen Carbonate. Mix for 2 minutes.
Stop the mixer and add the liquid flavours. Mix for 3 minutes.
Discharge into rolling bins and let stand for a minimum of 45 minutes.
Shaping and Polishing
Pass through rolling and scoring rollers to form sheets of centers (unpolished gum).
Let center sheets set up for at least 24 hours before polishing. The center sheets are then fed into a separator to break up the sheets into individual centers (unpolished gum pieces).
Discharge 422-507 Kgs of centers into a polishing pan.
Add Carnauba Wax to the polishing pan.
Polish gum for 20 minutes.
Discharge into storage containers for removal to the Packaging Line.

Stability

Using the procedure stated above the stability of the nicotine delivery product of the present invention was compared with the stability of the nicotine delivery product according to the state of the art. The results are stated in the below Table 12.

The samples have been stored under ambient conditions: storage in small containers with loose-fitting lid at laboratory temperature and humidity conditions (approx. 20° C. and 50% RH) for 2 weeks. The samples are analysed for content of nicotine, and the results are presented on anhydrous basis.

TABLE 12

| | Nicotine content % (anhydrous) | | |
|---|---|---|---|
| | At start | | After 2 weeks |
| Mixture | Added | found | found |
| Example 1 | 15.6 | 15.1 | 14.9 |
| Example 2 | 20 | 20.4 | 19.8 |
| Example 3 | 20 | 20.1 | 20.3 |
| Example 4 | 20 | 19.5 | 19.6 |
| Example 5 | 20 | 20.0 | 19.7 |
| Example 6 | 20 | 20.4 | 20.0 |
| Example 7 | 20 | 19.5 | 19.5 |
| Example 8 | 20 | 19.4 | 18.9 |
| Example 9 | 20 | 20.6 | 20.0 |
| Example 10 | 20 | 20.3 | 20.4 |

As it appears, the stability of the product of the invention is about the same as the stability of the nicotine delivery product according to the state of the art Stability Tests and Release Results in Chewing Gum The stability of the nicotine delivery product has been tested in chewing gum products.

A chewing gum product made according to example 12 containing a nicotine delivery product made according to example 1 (state of the art) and containing 2 mg nicotine have been tested for stability, stored in blister packs at 25° C./60% RH:

| | Month after production: | | | |
|---|---|---|---|---|
| Content of nicotine found: | 0 | 6 | 12 | 30 |
| Batch 0411F00058: | 2.08 | 2.04 | 2.08 | 2.02 |
| Batch 0512F00066: | 2.08 | 2.06 | 2.00 | 2.04 |

The release of nicotine after 30 min. from the two batches have been tested:

| | |
|---|---|
| Batch 0411F00058 | 80% |
| Batch 0512F00066 | 79% |

A chewing gum product made according to example 12, containing a nicotine delivery product made according to example 2 and containing 2 mg nicotine have been tested for stability, stored in blister packs at 25° C./60% RH:

| Content of nicotine found: | Month after production: | | |
|---|---|---|---|
| | 0 | 7 | 33 |
| Batch 5364-P51-2 | 1.9 | 1.9 | 1.9 |
| Batch 5388-P109-1 | 2.1 | | 2.0 |

The release of nicotine after 20 min. from the two batches have been tested:

| Batch 5364-P51-2 | 81% |
|---|---|
| Batch 5388-P109-1 | 76% |

A chewing gum product made according to example 12, containing a nicotine delivery product made according to example 3 and containing 2 mg nicotine have been tested for stability, stored in blister packs at 25° C./60% RH:

| Content of nicotine found: | Month after production: | | |
|---|---|---|---|
| | 0 | 6 | 30 |
| Batch 5364-P49-2 | 2.0 | 1.8 | 1.8 |
| Batch 5364-P50-2 | 2.0 | 1.9 | 1.9 |

The release of nicotine after 20 min. from the two batches have been tested:

| Batch 5364-P49-2 | 81% |
|---|---|
| Batch 5388-P50-2 | 84% |

As it appears, both the release and the stability of the product of the invention is about the same as the stability of the nicotine delivery product according to the state of the art.

The invention claimed is:

1. A method of producing a nicotine delivery product, the method comprising:
    combining (i) a mixture comprising nicotine, a cation exchange resin and water, wherein the water content of the mixture is between 5 and 75 wt. % relative to the whole mixture, wherein said mixture is a wet mixture and has a release rate of nicotine of at least 70% over a 10 minute period; and
    (ii) further components of the nicotine delivery product, wherein either the mixture (i) is produced by a method which comprises a step (a) of mixing nicotine, a cation exchange resin and water and a subsequent step (b) of removing up to 85 wt. % of the water, or wherein the mixture (i) is produced by a method which does not comprise a step of removing water;
    wherein the nicotine delivery product is selected from nicotine-containing chewing gums, nicotine-containing lozenges, nicotine-containing pastilles, nicotine-containing tablets and nicotine-containing patches.

2. The method according to claim 1 wherein the water content of the mixture is between 10 and 75 wt. %.

3. The method according to claim 1 wherein the cation exchange resin is selected from the group consisting of (i) a methacrylic, weakly acidic type of resin containing carboxylic functional groups (ii) a polystyrene, strongly acidic type of resin containing sulphonic functional groups, and (iii) a polystyrene, intermediate acidic type of resin containing phosphonic functional groups.

4. The method according to claim 1, wherein the concentration of nicotine in the mixture is between 5 and 50 wt. %.

5. The method according to claim 1, wherein the weight ratio of cation exchange resin to nicotine in the mixture is from 1:1 to 10:1.

6. The method according to claim 1, wherein the mixture (i) further comprises an organic polyol which is a C2 to C12 linear or branched hydrocarbon having at least 2 hydroxyl groups.

7. The method according to claim 1 wherein up to 80 wt. % of water is removed in step (b).

8. The method according to claim 1 wherein an organic polyol which is a C2 to C12 linear or branched hydrocarbon having at least 2 hydroxyl groups, is combined with a first pre-mix comprising nicotine and the cationic exchange resin.

9. The method according to claim 1 further comprising the addition of a second pre-mix, wherein an organic polyol which is a C2 to C12 linear or branched hydrocarbon having at least 2 hydroxyl groups, is combined with the second pre-mix comprising the cation exchange resin, said second pre-mix being free of nicotine.

10. The method according to claim 1 wherein the nicotine delivery product is a nicotine-containing chewing gum formulation, and wherein the further components (ii) comprise a gum base and a sweetener.

* * * * *